United States Patent
Aval et al.

(10) Patent No.: US 6,554,471 B2
(45) Date of Patent: Apr. 29, 2003

(54) THERMOTHERAPY APPARATUS WITH RETRACTABLE RECLINING SURFACE

(75) Inventors: Petra Aval, Lübeck (DE); Thomas Bohnen, Lübeck (DE); Michael Geier, Lübeck (DE); Ralf Graute, Lübeck (DE); Hans-Joachim Kannengiesser, Lübeck (DE); Edeltraud Meyer, Ahrensbök (DE); Karsten Scharnweber, Ahrensbök (DE)

(73) Assignee: Dräger Medizintechnik GmbH (DE)

( * ) Notice: Subject to any disclaimer, the term of this patent is extended or adjusted under 35 U.S.C. 154(b) by 100 days.

(21) Appl. No.: 09/850,340

(22) Filed: May 7, 2001

(65) Prior Publication Data

US 2002/0003865 A1 Jan. 10, 2002

(30) Foreign Application Priority Data

May 9, 2000 (DE) .......................................... 100 22 320
Dec. 13, 2000 (DE) .......................................... 100 62 127

(51) Int. Cl.$^7$ ............................................... G01N 21/34
(52) U.S. Cl. ....................................................... 378/177
(58) Field of Search ................................. 378/177–179

(56) References Cited

U.S. PATENT DOCUMENTS 3,997,792 A * 12/1976 Conrad et al. ............... 378/177

* cited by examiner

Primary Examiner—Craig E. Church
(74) Attorney, Agent, or Firm—McGlew and Tuttle, P.C.

(57) ABSTRACT

A thermotherapy apparatus has a reclining surface (3) and an X-ray drawer (6) that can be retracted from the apparatus together when needed. A carrier (12) is located at the X-ray drawer (6) and can be connected to the reclining surface (3) in a preferred position.

20 Claims, 5 Drawing Sheets

THERMOTHERAPY APPARATUS WITH RETRACTABLE RECLINING SURFACE

FIELD OF THE INVENTION

The present invention pertains to a thermotherapy apparatus with a reclining surface for a patient.

BACKGROUND OF THE INVENTION

Thermotherapy apparatuses have been known from the state of the art which have as the individual components a retractable reclining surface, an X-ray drawer located under the reclining surface, scales for determining the patient's weight, as well as a heater for the reclining surface.

No thermotherapy apparatus which combines all four functions is available in the state of the art. The individual components are disadvantageous for the following reasons:

The available X-ray drawers can be opened only when a front flap or a side panel is opened. This causes a disturbance for the patient in both cases because the climate is compromised. The available scales are auxiliary devices which must be placed into the space of the patient and therefore also must be cleaned during preparation.

If the scales are located under the reclining surface, problems may arise when the reclining surface is sloped in relation to the scales.

If the scales are located directly under the reclining surface, X-raying must be performed through the scales. There is no heated reclining surface so far which is transparent to X-rays without distorting the X-ray image.

SUMMARY AND OBJECTS OF THE INVENTION

The object of the present invention is to improve a thermotherapy apparatus of this type such that the reclining surface and an X-ray drawer located under the reclining surface can be retracted from the apparatus together when needed.

According to the invention, a thermotherapy apparatus with a reclining surface for a patient is provided with a displaceable drawer. The displaceable drawer is located under the reclining surface. An adjustable carrier is located at the drawer and can be connected to the said reclining surface in a preferred position.

The advantage of the present invention is essentially that the drawer can be connected to the reclining surface if necessary by means of a pivotable carrier located at the drawer, so that the drawer and the reclining surface can be pulled together out of the housing of the thermotherapy apparatus. If the carrier is positioned such that there is no connection to the reclining surface, the drawer can be actuated independently from the reclining surface. The carrier advantageously is hook-shaped or is in the form of an oval cam disk, so that in the preferred position, in which the reclining surface and the drawer shall be pulled together out of the thermotherapy apparatus, it reaches under the reclining surface and slightly raises same.

A projection may be provided fixing the carrier. The projection is arranged at the reclining surface. The reclining surface may be fastened on four supports of scales (i.e., a scale or weight measuring device). The drawer may be arranged displaceably between supports in a housing encompassing the said reclining surface. A heater comprised of carbon fibers, may be fastened to the reclining surface. The carrier may have an arc shaped circumferential contour such that the reclining surface is separated from the supports in the preferred position of the carrier.

The drawer is advantageously the x-ray drawer. The support point of the reclining surface may be designed as a crater-shape (concave) depression. Another support point may be provided with a groove-shape design offering a defined position in one direction only. The other support points may advantageously be surfaces without lateral fixation. Further, by providing the carrier with an arc-shaped, preferably hook-shaped circumferential contour, the support points of the reclining surface may be separated from the supports of the scales and the preferred position of the carrier.

It is particularly advantageous to provide a projection under the reclining surface in the pivoting range of the carrier such that in the preferred position, the carrier is in contact with the rear side of the projection and thus there is a connection between the reclining surface and the X-ray drawer. As an alternative to a projection, the reclining surface may be provided in the pivoting range of the carrier with a milled recess, which is engaged by the carrier in the preferred position.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
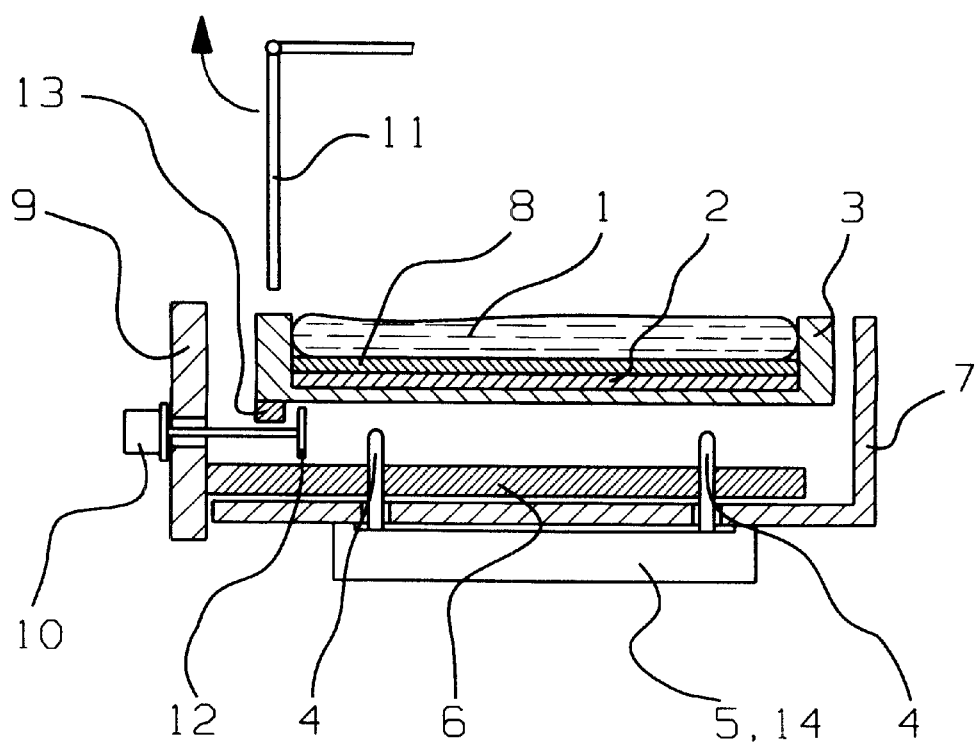
FIG. 1 is a detail longitudinal sectional view of a thermotherapy apparatus.

The embodiment shown in FIG. 1 provides an thermotherapy arrangement (e.g., patent warmer, infant warmer or incubator) which makes possible a minimal interaction of the functions. The heater 2 in the form of a heating foil consisting of carbon fibers is bonded into the reclining surface 3. The heating foil is protected with a plastic plate 8 against mechanical damage. A gel mattress 1 lies on it. The reclining surface 3 rests on four supports 4, which are in turn supported on two weighing elements 5. The weighing elements 5 are located under the supporter housing 7, i.e., they are not located in the area that is to be cleaned. The X-ray drawer 6 is located directly under the reclining surface 3, so that only the components of the reclining surface 3 are X-rayed.

When pulling the grip 9, it must be decided by means of a rotary knob 10 whether the reclining surface is to be retracted with the patient or whether the X-ray drawer 6 is to be retracted separately.

An engagement device or carrier 12, which is connected to the rotary knob 10 and engages from behind a projection 13 located on the reclining surface 3, is provided for this purpose. The X-ray drawer 6 and the reclining surface 3 are retracted together in the position of the carrier 12 shown in FIG. 1. In another position of the carrier 12, the X-ray drawer 6 can be actuated independently from the reclining surface 3. The patient on the reclining surface 3 can be retracted only with the front flap 11 opened. The patient is not shown in FIG. 1 for the sake of greater clarity.

Figure 2:
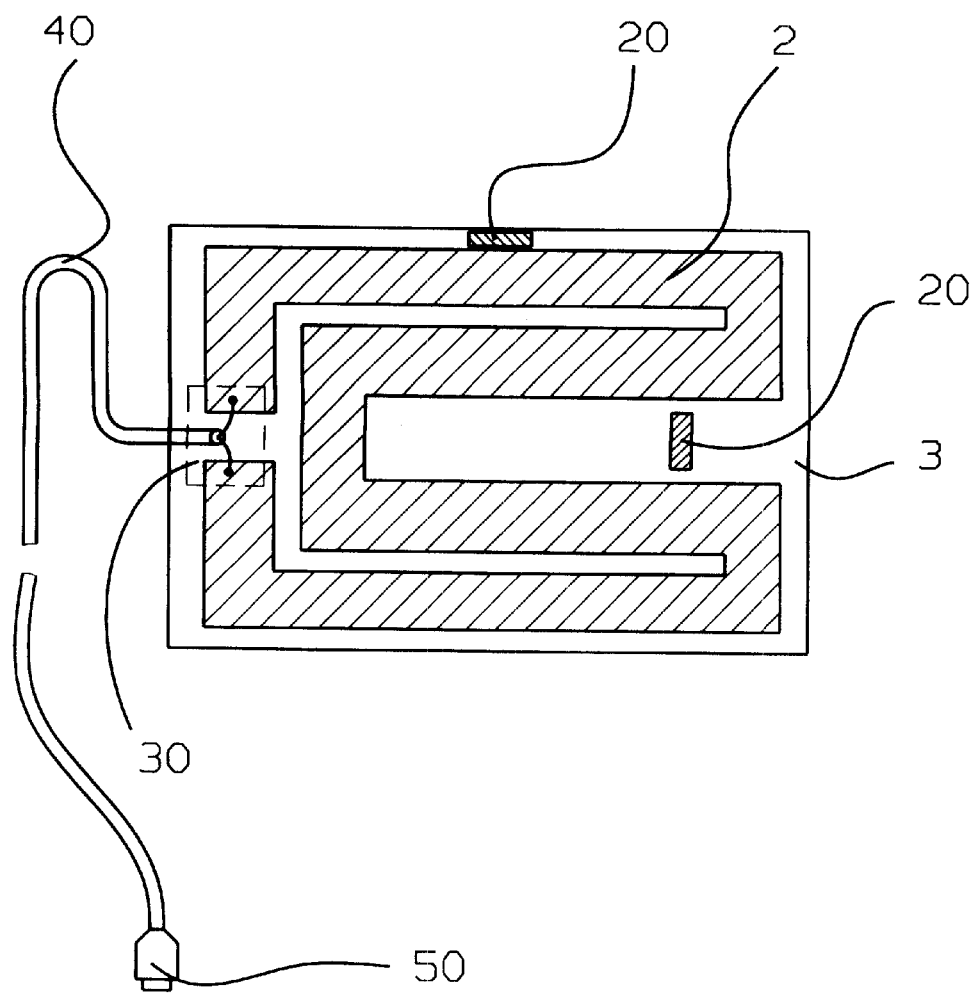
FIG. 2 is a top view of the heater of the reclining surface.

The reclining surface 3 is heated by the heater 2 in the form of an electric resistance heater. The conductive material, carbon fiber, has a layer thickness of approx. 1.0 mm. The strips of the heater 2 are located on the reclining surface 3 in a meander-shaped pattern, FIG. 2. These strips are not visible in the X-ray image because of the material selected. The sensors 20 necessary for the temperature control in the reclining surface 3 are likewise arranged such that they are not visible in an X-ray image. The requirements concerning the uniformity of the heat distribution are met with this arrangement.

The connection point 30 between the heater 2 and the connection cable 40 is embedded to eliminate the risk of spark formation in the space enriched with oxygen. The cable 40 is laid in a loop to the basic housing. This makes it possible, on the one hand, to retract the reclining surface 3 and, on the other hand, it ensures a very low shunt of forces, which would affect the weighing. The plug-type connection 50 for connect the heater 2 to a control device, not shown in the figures, and to the power supply of the thermotherapy apparatus, (e.g., incubator patient warmer, infant warmer) is outside the patient space and thus outside the space enriched with oxygen.

Figure 3:
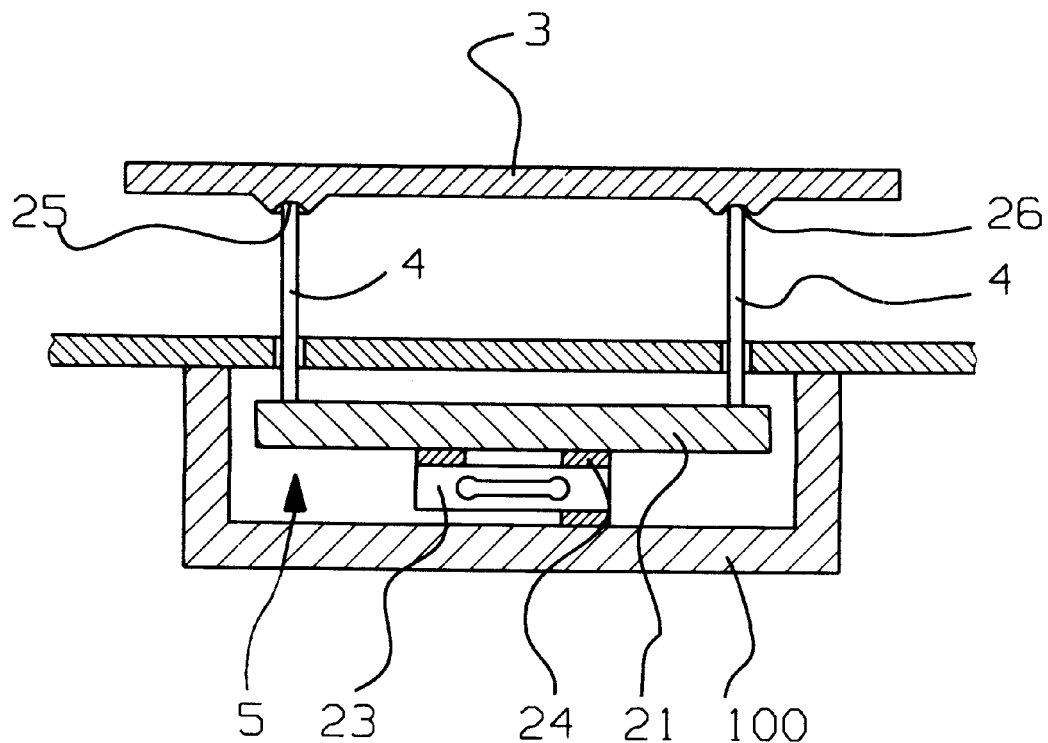
FIG. 3 is a longitudinal sectional view of scales for a reclining surface at right angles to the view in FIG. 1.

The scales, not shown in greater detail in the figures, comprise two weighing elements 5 of identical design, FIG. 3, which are mounted in the housing 100 of the apparatus.

A weighing element 5 comprises a transverse bar 21 with the. supports 4 and a weighing cell 23. The second weighing element, which has a design corresponding to the weighing element 5, is not shown in FIG. 3. Thus, the reclining surface 3 lies on four points of the scales formed by the weighing elements 5. To prevent the weighing cells 23 from being overloaded, the weighing cells 23 have a stop 24, which offers protection against overload. No element of the scales may have a shunt of forces on a part of the housing 100 or other parts, because this would distort the measurement. To also achieve this in the case of a retractable reclining surface 3, one support point 25 of the reclining surface 3 is designed as a crater-shaped depression, while another support point 26 is groove-shaped and offers a defined position in one direction only. The other two support points, not shown in FIG. 3, are surfaces which have no lateral fixation whatsoever. Due to the oblique surfaces, which are not shown in FIG. 3 and lead to the respective deepest points of the support points 25, 26, the reclining surface 3 finds the last section of travel, approx. 4 mm, by itself. Thus, it slides into the position in which it is at a spaced location on all sides which does not permit a shunt of forces.

The X-ray drawer 6, FIG. 1, is located under the reclining surface 3 and runs in a guide of the housing 7. There is no contact between the X-ray drawer 6 and the reclining surface 3 in the initial state, when the carrier 12 is not located behind the projection 13. The scales can be used and the X-ray drawer 6 can be pulled out and pushed in in this state. If the reclining surface 3 is to be retracted, the rotary knob 10 shall be turned to the extent that the carrier 12 engages the projection 13 of the reclining surface 3 from behind. Due to the hook-shaped design of the carrier 12, the reclining surface 3 is slightly raised during the turning of the rotary knob 10. Thus, the reclining surface 3 does not have to be pulled from the scales over the supports 4 during retraction.

Figure 4:
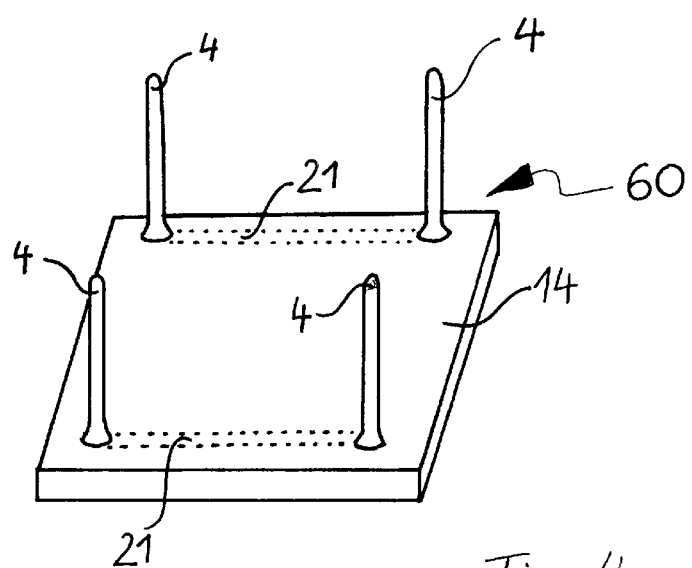
FIG. 4 is a perspective top view of the scales.

FIG. 4 shows scales 60, which comprise a basic body 14 containing the weighing elements 5, (see also FIG. 3), and the supports 4 extending therefrom upward at right angles. Two supports 4 each are connected via the transverse bars 21 extending in the basic body 14. The basic body 14 contains the housing 100 of the apparatus and a cover plate, not shown in FIG. 3, which is located above the housing 100 of the apparatus.

Figure 5:
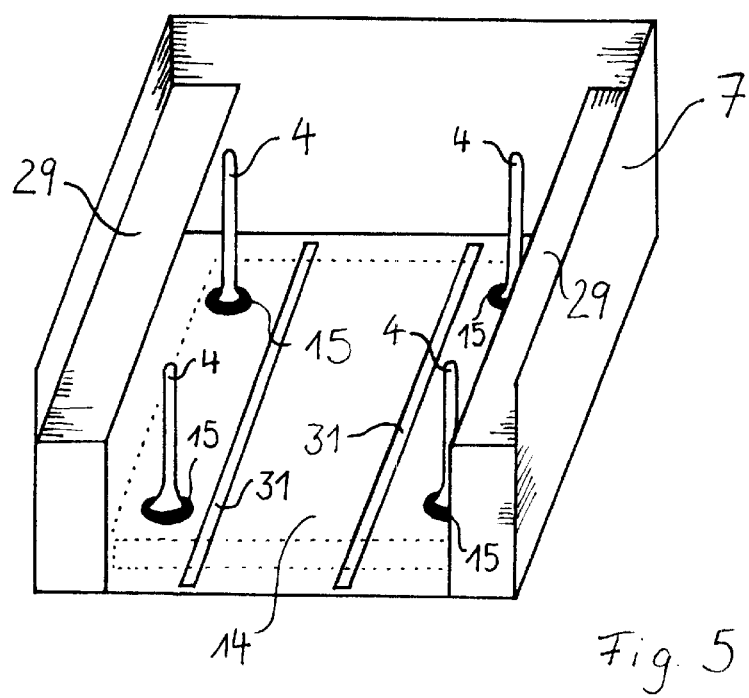
FIG. 5 is a perspective view showing the scales with a housing arranged thereon.

FIG. 5 shows the scales 60, (see also FIG. 4), with the housing 7 arranged thereon. Each support 4 of the scales extends from below through a corresponding hole 15 in the bottom of the housing 7 and extends therefrom vertically upward into the interior of the housing 7. The X-ray drawer 6, (see FIG. 6), runs on a guide 31 of the housing 7. The reclining surface 3, (see FIG. 7), runs on a guide 29 and is also guided by the lateral outer walls of the housing 7.

Figure 6:
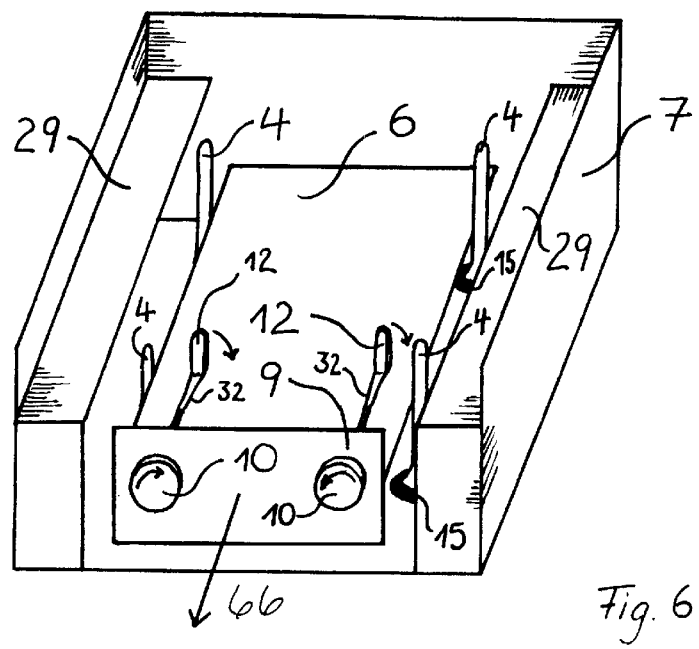
FIG. 6 is a perspective view showing the scales with the housing and an X-ray drawer located in the housing.

The scales 60, (see FIG. 4), with the housing 7 arranged thereon and with the X-ray drawer 6 located in the housing 7 is shown in FIG. 6. The X-ray drawer 6 can be pulled out of the housing 7 horizontally forward in the direction of arrow 66. It is dimensioned in its horizontal extension at right angles to the direction of pull indicated by arrow 66 such that it finds space between the supports 4 protruding vertically into the interior of the housing 7 and can be opened and closed unhindered by the supports 4. At its front toward the outer side of the housing 7, the X-ray drawer 6 is limited by the grip 9. Two rotary knobs 10, which are connected to a carrier 12 each via connecting rods 32 through the front surface of the grip 9, are located on the grip 9. The carriers 12 are bent in a hook-shaped manner from the connection rods 32, pointing in the direction of the free ends of the supports 4.

Figure 7:
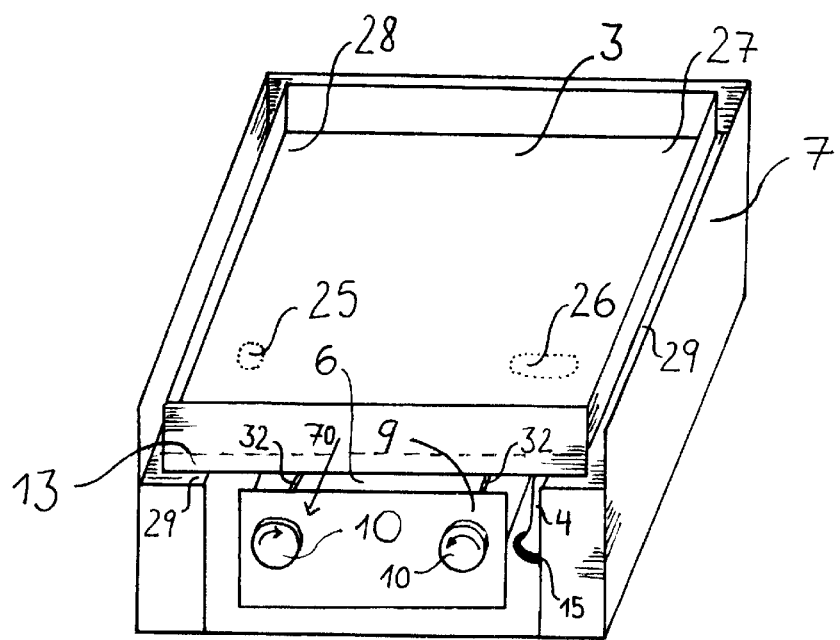
FIG. 7 is a perspective view showing the device according to FIG. 6 with the reclining surface arranged thereon.

FIG. 7 shows the scales 60, (see also FIG. 4), with the housing 7 arranged thereon and with the X-ray drawer 6 located in the housing 7 with the reclining surface 3 arranged on the X-ray drawer. Only the front part of the X-ray drawer 6 can be seen in FIG. 7 in the area of the grip 9, because it is covered by the reclining surface 3. The support points 25, 26, 27 and 28 each receive one of the supports 4. The support point 25 has a crater-shaped design. The support point 26 has a groove-shaped design in the form of an oval groove. The support points 25, 26, 27 and 28 are located on the underside of the bottom of the reclining surface 3. The support points 25 and 26 are indicated by broken lines in FIG. 7. The other two support points 27 and 28 are surfaces which have no lateral fixation. A shunt of forces between the reclining surface 3 and the housing 7 is avoided due to this design of the support points 25, 26, 27, 28.

The reclining surface 3 runs on a guide 29 and is also guided on the sides by the walls of the housing 7. The housing 7 is open to the front in order to make it possible to pull out the reclining surface 3 in the direction of arrow 70.

Before the grip 9 is pulled, it is determined by setting the two rotary knobs 10 whether the X-ray drawer 6 will be pulled out separately or whether the X-ray drawer 6 will be pulled out together with the reclining surface 3.

The rotary knobs 10 are connected to the carriers 12 via the connecting rods 32, so that the carriers 12 bent off in a hook-shaped manner from the connecting rods 32 can assume either a horizontal position by rotating the rotary knobs 10 in the direction of the arrow or a vertical position, pointing in the direction of the free ends of the supports 4, as is shown in FIG. 6, by rotating the rotary knobs 10 against the direction of the arrow.

If the carriers 12 are in the horizontal position, the X-ray drawer 6 can be pulled out separately.

If the carriers 12 are in the vertical position, they engage the projection 13 located at the reclining surface 3 from behind. The X-ray drawer 6 and the reclining surface 3 are pulled out together. The length of the carriers 12 is selected to be such that the carriers slightly raise the reclining surface 3 in the vertical position. The reclining surface 3 will then no longer lie on the support points 25 and 26, but on the free ends of the carriers 12. Thus, the crater-shaped depression of the support point 25 and the groove-shaped depression of the support point 26 do not have to be pulled over the supports 4, which would lead to jerky movements of the reclining surface and consequently to a disturbance for the patient.

While specific embodiments of the invention have been shown and described in detail to illustrate the application of the principles of the invention, it will be understood that the invention may be embodied otherwise without departing from such principles.

What is claimed is:

1. A thermotherapy apparatus, comprising:
   a support;
   a reclining surface for a patient supported by said support and movable relative to said support;
   a displaceable drawer located under said reclining surface and displaceable relative to said support; and
   an adjustable carrier located adjacent to said drawer and connectable to said reclining surface in a connection position for moving said reclining surface with said drawer upon displacing said drawer.

2. A thermotherapy apparatus in accordance with claim 1, wherein said drawer is a X-ray drawer.

3. A thermotherapy apparatus in accordance with claim 1, further comprising a projection associated with said reclining surface for connecting said carrier to said reclining surface, said projection being arranged at or adjacent to said reclining surface.

4. A thermotherapy apparatus in accordance with claim 2, further comprising a projection associated with said reclining surface for connecting said carrier, said projection being arranged at or adjacent to said reclining surface.

5. A thermotherapy apparatus in accordance with claim 1, further comprising a scale with supports, wherein said reclining surface is engagable on said supports of said scale.

6. A thermotherapy apparatus in accordance with claim 5, wherein said support comprises a housing, wherein said drawer is arranged displaceably between said supports of said scale in said housing, said housing extending around at least a portion of said reclining surface.

7. A thermotherapy apparatus in accordance with claim 5, wherein said reclining surface lies on a plurality of supports of said scale.

8. A thermotherapy apparatus in accordance with claim 7, said supports include a support point of said reclining surface with a crater-shaped depression and another support point with a groove-shape to provide a defined position in one direction only, and other support points having surfaces without lateral fixation.

9. A thermotherapy apparatus in accordance with claim 6, wherein said housing contains said reclining surface, wherein said drawer is a X-ray drawer displaceably positioned between said supports, said drawer being arranged in said housing.

10. A thermotherapy apparatus in accordance with claim 1, further comprising a heater, said heater including carbon fibers fastened to said reclining surface.

11. A thermotherapy apparatus in accordance with claim 5, wherein said carrier has an arc-shaped circumferential contour such that support points of said reclining surface are separated from said supports of said scale in a preferred position of said engagement device.

12. A medical treatment arrangement, comprising:
    a support;
    a reclining surface for a patient, said reclining surface being supported by said support and movable relative to said support;
    a displaceable drawer, which is located under said reclining surface and displaceable relative to said support; and
    an engagement device connected to said drawer and connectable to said reclining surface in an engagement position of said engagement device for moving said reclining surface with said drawer, with said engagement device in said engagement position, upon displacing said drawer.

13. A thermotherapy apparatus in accordance with claim 12, further comprising a projection associated with said reclining surface for connecting said engagement device to said reclining surface, said projection being arranged at or adjacent to said reclining surface.

14. A thermotherapy apparatus in accordance with claim 12, further comprising a scale, wherein said reclining surface is fastened on supports of said scale.

15. A thermotherapy apparatus in accordance with claim 12, wherein said support is a housing containing said reclining surface, wherein said drawer is arranged displaceably between said supports in said housing.

16. A thermotherapy apparatus in accordance with claim 12, further comprising a heater, said heater including carbon fibers fastened to said reclining surface.

17. A thermotherapy apparatus in accordance with claim 14, wherein said engagement device has an arc-shaped circumferential contour such that said reclining surface is separated from said supports in a preferred position of said carrier.

18. A medical treatment arrangement, comprising:
    a support;
    a reclining surface for a patient, said reclining surface being supported by said support and movable relative to said support;
    a displaceable X-ray drawer, which is located under said reclining surface and displaceable relative to said support; and
    an engagement device connected to said drawer and connectable to said reclining surface in an engagement position of said engagement device for moving said reclining surface with said drawer, with said engagement device in said engagement position, upon displacing said drawer; and
    a heater, said heater including carbon fibers fastened to said reclining surface.

19. A medical treatment arrangement apparatus in accordance with claim 18, further comprising a scale, wherein said reclining surface is fastened on supports of said scale.

20. A medical treatment arrangement apparatus in accordance with claim 19, wherein said support is a housing receiving at least a portion of said reclining surface and wherein said drawer is arranged displaceably between said supports in said housing.

* * * * *